United States Patent [19]

Connell et al.

[11] Patent Number: 5,317,078
[45] Date of Patent: May 31, 1994

[54] POLYBENZIMIDAZOLE VIA AROMATIC NUCLEOPHILIC DISPLACEMENT

[75] Inventors: John W. Connell; Paul M. Hergenrother, both of Yorktown; Joseph G. Smith, Hampton, all of Va.

[73] Assignee: The United States of America as represented by the Administrator of the National Aeronautics and Space Administration, Washington, D.C.

[21] Appl. No.: 790,730

[22] Filed: Oct. 30, 1991

[51] Int. Cl.⁵ .............................. C08G 73/18
[52] U.S. Cl. .................. 528/210; 528/125; 528/128; 528/171; 528/172; 528/174; 528/183; 528/185; 528/186; 528/191; 528/208; 528/219; 528/220; 528/228; 548/312.7
[58] Field of Search ........... 528/210, 208, 183, 185, 528/186, 191, 219, 125, 128, 171, 172, 174, 220, 228

[56] References Cited

U.S. PATENT DOCUMENTS 5,039,778  8/1991  Dang et al. ............... 528/210

Primary Examiner—Harold D. Anderson
Attorney, Agent, or Firm—George F. Helfrich

[57] ABSTRACT

Di(hydroxyphenyl)benzimidazole monomers were prepared from phenyl-4-hydroxybenzoate and aromatic bis(o-diamine)s. These monomers were used in the synthesis of soluble polybenzimidazoles. The reaction involved the aromatic nucleophilic displacement of various di(hydroxyphenyl)benzimidazole monomers with activated aromatic dihalides or activated aromatic dinitro compounds in the presence of an alkali metal base. These polymers exhibited lower glass transition temperatures, improved solubility, and better compression moldability over their commercial counterparts.

9 Claims, No Drawings

POLYBENZIMIDAZOLE VIA AROMATIC NUCLEOPHILIC DISPLACEMENT

ORIGIN OF THE INVENTION

The invention described herein was jointly made by employees of the U.S. Government and a contract employee in the performance of work under NASA Grant No. NAG1-448 and is subject to the provisions of Public Law 96-517 (35 USC 202) in which the contractor has elected not to retain title.

BACKGROUND OF THE INVENTION

1. Field of the Invention

The present invention relates generally to polybenzimidazoles. In particular, it relates to polybenzimidazoles prepared by the aromatic nucleophilic displacement reaction of di(hydroxyphenyl)benzimidazole monomers with activated aromatic dihalides or activated dinitro compounds.

2. Description of the Related Art

Polybenzimidazoles (PBIs) are heterocyclic macromolecules commonly prepared by the condensation reaction of an aromatic bis(o-diamine) with an aromatic diacid or derivative thereof. These polymers possess high thermal, thermooxidative, and chemical stability; good mechanical properties; and excellent flame resistance, making them high-performance/high-temperature materials which are attractive for use in harsh environments. However, despite these properties, the processing of these polymers is somewhat difficult.

Buckley et al (*Encyclopedia of Polymer Science and Technology*, Volume 11, 2nd Ed., 1988, p.572) review polybenzimidazoles. They specifically review poly[2,2'-(m-phenylene)-5,5'-bibenzimidazole], which is commercially available primarily from Hoechst-Celanese Corporation. The processing of this material involves two steps: the formation of a foam which must be ground into a powder and reheating of the PBI powder. This polymer is mainly used in the formation of fibers because it is not very soluble in solvent. For example, in order to dissolve the PBI in dimethylacetamide (DMAc), both the solvent and the polymer had to be heated under pressure. The glass transition temperatures (Tg) of this polymer is 435° C. Because of this high Tg, the polymer is difficult to compression and injection mold.

Several methods have been used to prepare PBIs. Brinker and Robinson (U.S. Pat. No. 2,895,948) synthesized PBIs by reacting aliphatic dicarboxylic acids with aromatic bis(o-diamine)s. Vogel and Marvel (*Journal of Polymer Science*, 50, 511 (1961)) formed PBIs from the melt condensation of aromatic bis(o-diamine)s with aromatic diacids or derivatives thereof. Iwakura et al (*Journal of Polymer Science*, Part A, 2, 2605, (1964)) prepared PBIs in polyphosphoric acid. Hedberg and Marvel (*Journal of Polymer Science, Polymer Chemistry*, 12, 1823 (1974)) formed PBIs in sulfolane or diphenylsulfone from aromatic bis(o-diamine)s and aromatic diacids or derivatives thereof. Another preparative route by Higgins and Marvel (*Journal of Polymer Science*, Part A-1, 8, 171 (1970)) involves the reaction of aromatic bis(o-diamines)s with the bis(bisulfite adduct)s of dialdehydes. Packham et al (*Polymer*, 10 (12), 923 (1969)) formed PBIs from the alkoxide catalyzed reaction of aromatic bis(o-diamine)s with dinitriles. None of these methods teach the preparation of PBIs by the reaction of di(hydroxyphenyl)benzimidazole monomers with activated aromatic dihalide or dinitro compounds in the presence of an alkali metal base.

SUMMARY OF THE INVENTION

Several di(hydroxyphenyl)benzimidazole monomers were prepared from the reaction of phenyl-4-hydroxybenzoate with aromatic bis(o-diamine)s. These monomers have the following structural formulas:

a) 5,5'-Bis[2-(4-hydroxyphenyl)benzimidazole

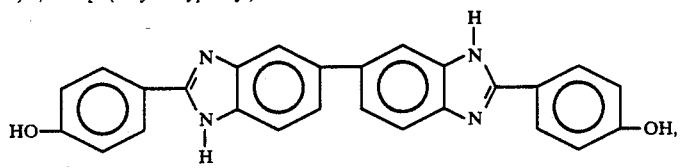

b) 5,5'-Carbonyl-bis[2-(4-hydroxyphenyl)benzimidazole

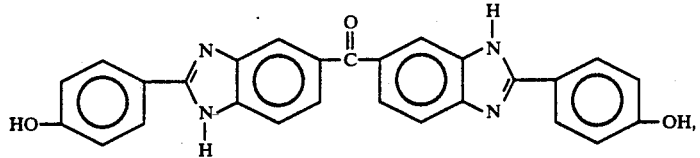

c) 5,5'-Oxy-bis[2-(4-hydroxyphenyl)benzimidazole

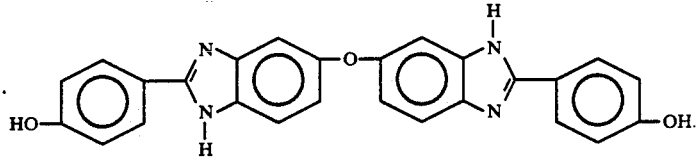

Soluble polybenzimidazoles (PBIs) were then prepared by the nucleophilic displacement reaction of these di(hydroxyphenyl)benzimidazole monomers with activated aromatic dihalide or dinitro compounds in the presence of an alkali metal base. The resulting PBIs had the following general structural repeat units:

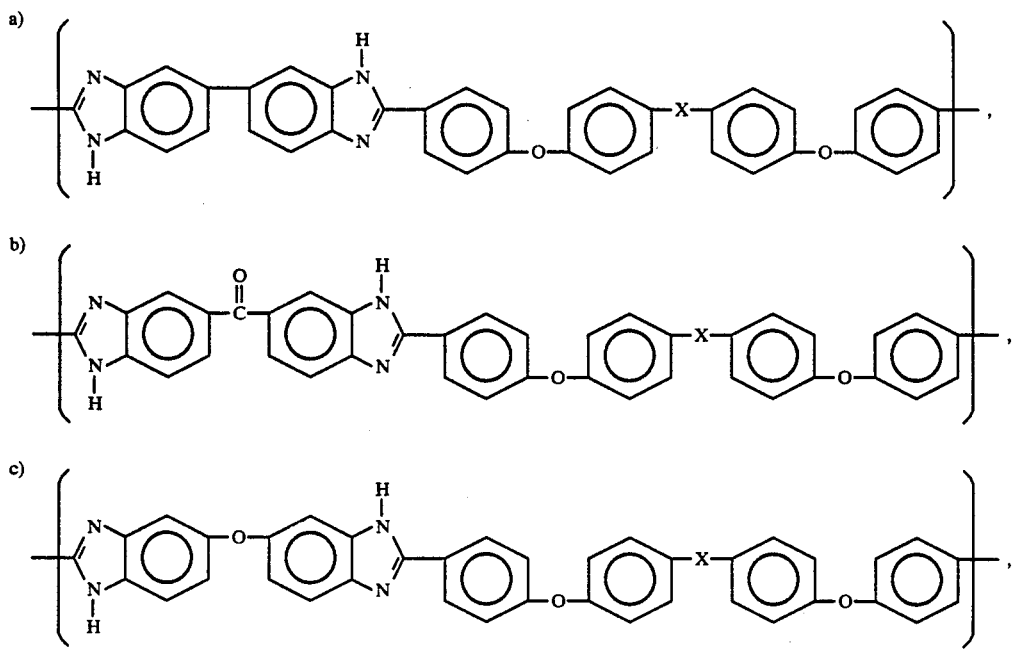

where x is

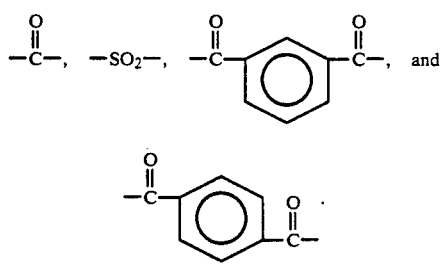

These polymers had glass transition temperatures (Tg) ranging from 264° to 352° C., much lower than their commercial counterparts which exhibited Tgs of 400° C. As a result of the lower Tgs, these polymers exhibited much better compression moldability than other PBIs. These polymers were found to be soluble in cold DMAc, as opposed to requiring hot DMAc and pressure to solubilize. The use of benzimidazole monomers to make PBIs proved to be more economical and easier to process than commercial PBIs without showing a loss in their physical and mechanical properties.

An object of the present invention is to prepare di(hydroxyphenyl)benzimidazole monomers.

Another object of the present invention is to prepare soluble polybenzimidazoles.

Another object of the present invention is to develop a new process for preparing soluble polybenzimidazoles.

Another object of the present invention is to prepare films from the soluble polybenzimidazoles.

DESCRIPTION OF THE PREFERRED EMBODIMENTS

The synthesis of soluble PBIs involved the use of di(hydroxyphenyl)benzimidazole monomers. These monomers were prepared by reacting phenyl-4-hydroxybenzoate with various aromatic bis(o-diamine)s. These monomers have the following general structural formula:

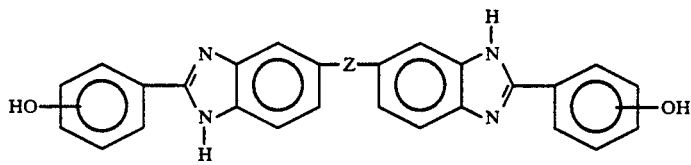

where z is either nil, —CH$_2$—, —O—, —S—,

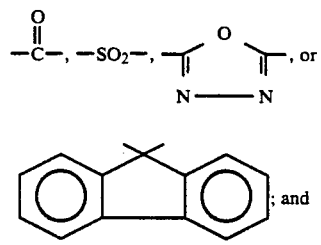

the catenation of the hydroxy groups may be meta-meta, para-para, or para-meta.

These benzimidazole monomers undergo a nucleophilic displacement reaction with activated aromatic dihalide or dinitro compounds in the presence of an alkali metal base such as: potassium carbonate, sodium carbonate, potassium hydroxide, and sodium hydroxide. The resulting PBIs are soluble in DMAc and have the following general structural repeat unit:

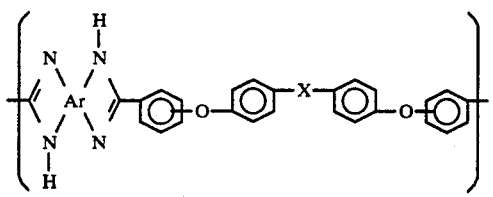

where:
the catenation of oxygen is either meta-meta, para-para, or para-meta;
Ar is any one of the following:

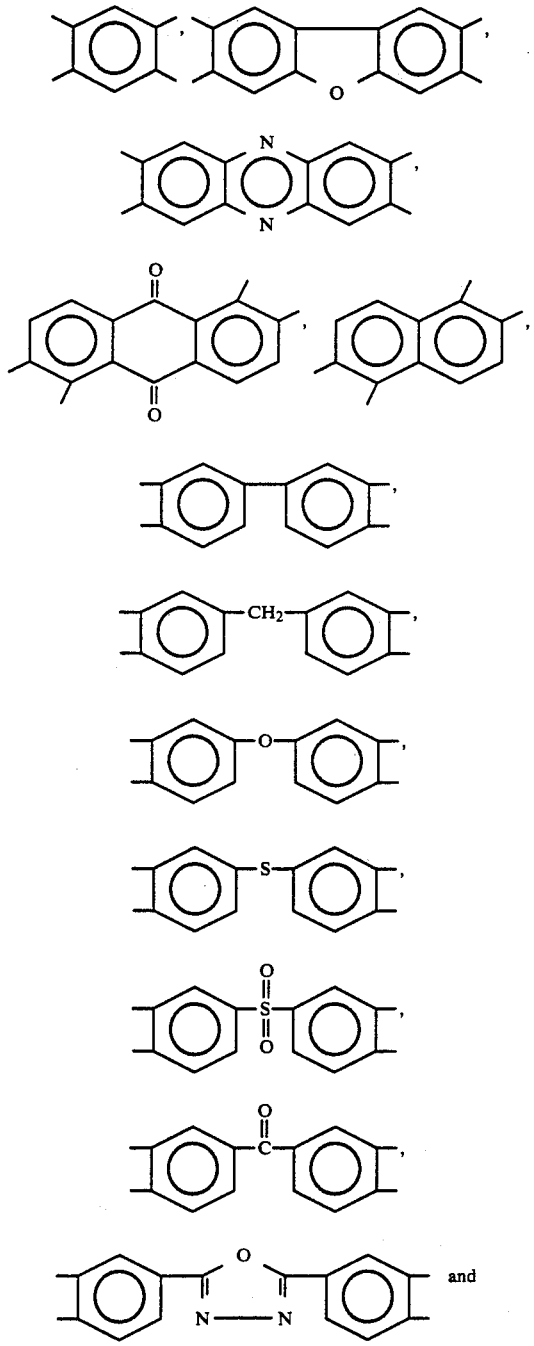

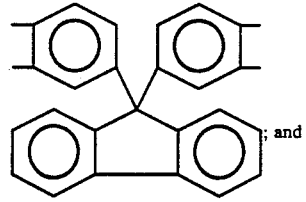

x is any one of the following:

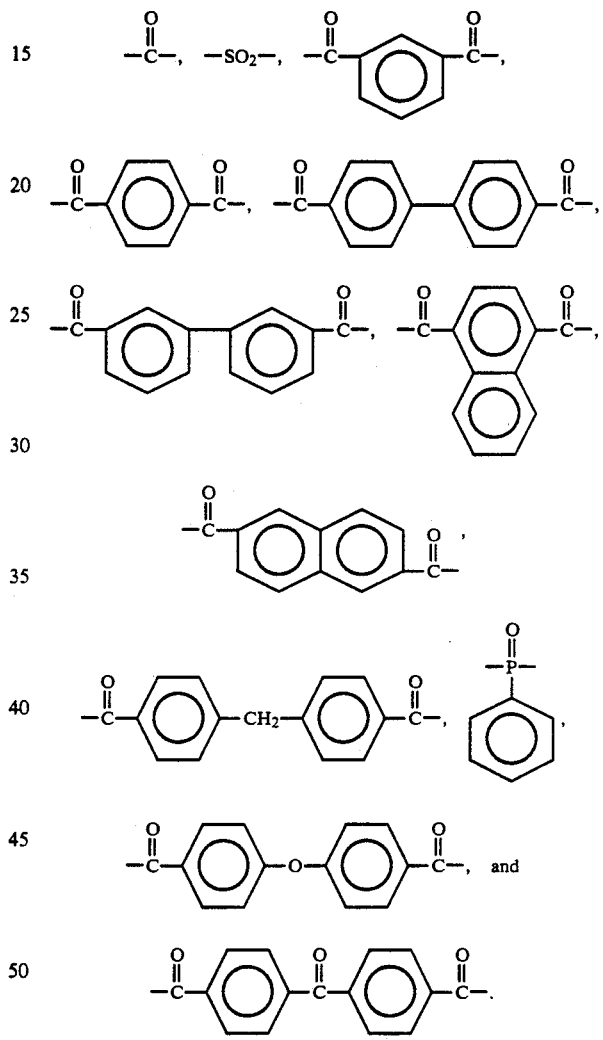

The solubility of these polymers allows for film formation, something which was difficult to achieve in previous PBI systems. These polymers also exhibited lower Tgs which makes compression and injection molding much easier.

The following examples are illustrative of the invention.

EXAMPLE 1

Preparation of the di(hydroxyphenyl)benzimidazole monomers 5,5'-Bis[2-(4-hydroxyphenyl)benzimidazole]

A mixture of 3,3',4,4'-tetraaminobiphenyl (commercially available from Hoechst-Celanese Corporation)

(25.80 g, 0.120 mol), phenyl-4-hydroxybenzoate (commercially available from K and K Laboratories) (52.62 g, 0.246 mol), diphenylsulfone (95.30 g), and toluene (100 ml) was heated under a nitrogen atmosphere for 2.5 hours at 150° C. The toluene was removed and the temperature increased to 250° C. and maintained for 0.75 hour. The reaction mixture solidified to a yellow mass. A vacuum was subsequently applied and the temperature increased to 280° C. and maintained for 1.25 hours. The cooled brown reaction mixture was washed successively in hot acetone and toluene and subsequently dried at 110° C. to afford 48.90 g (97% crude yield) of a brown powder. The melting endothermic peak as determined by differential thermal analysis (DTA) at a heating rate of 10° C./min was 404° C. (sharp). The solid was recrystallized twice from N,N-dimethylacetamide (DMAc) using charcoal to afford a tan powder (28.37 g, 56% yield). The compound exhibited a broad endothermic peak by DTA with a minimum at 398° C. Analysis calcd. for $C_{26}H_{18}N_4O_2$: C, 74.63%; H, 4.34%; N, 13.39%. Found: C, 73.31%; H, 4.32%; N, 13.26%. The resulting monomer had the following structural formula:

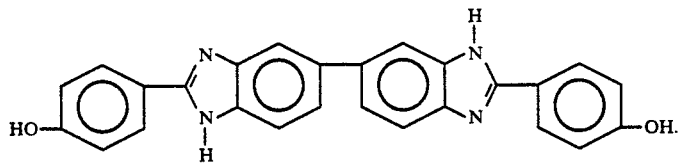

5,5'-Carbonyl-bis[2-(4-hydroxyphenyl)benzimidazole]

A mixture of 3,3',4,4'-tetraaminobenzophenone (commercially available from Burdick and Jackson) (22.61 g, 0.093 mol), phenyl-4-hydroxybenzoate (40.01 g, 0.187 mol), diphenylsulfone (110.45 g), and toluene (135 ml) was heated under a nitrogen atmosphere for 3 hours at 150° C. The toluene was removed and the temperature increased to 250° C. and maintained for 1.25 hours. A vacuum was subsequently applied and the temperature increased to 270° C. and maintained for 1 hour. The cooled yellow reaction mixture was washed successively in hot toluene and water and subsequently dried at 110° C. to afford 39.83 g (96% crude yield) of a yellow powder. The endothermic peak as determined by DTA was 387° C. (broad). The yellow solid was dissolved in DMAc, treated with activated charcoal, filtered, and poured into water to afford a yellow precipitate. The solid was dried under vacuum at 245° C. to afford 31.52 g (76% yield) of a brown powder. The endothermic peak as determined by DTA was 346° C. (broad). Analysis calcd. for $C_{27}H_{18}N_4O_3$: C, 72.64%; H, 4.06%; N, 12.55%. Found: C, 71.96%; H, 4.20%; N, 12.42%. The resulting monomer had the following structural formula:

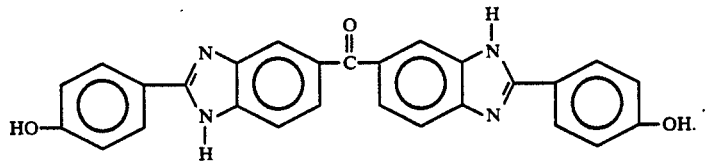

5,5'-Oxy-bis[2-(4-hydroxyphenyl)benzimidazole]

Oxydianaline was acetylated, nitrated, and the acetylated group hydrolyzed to give 3,3'-dinitro-4,4'-diaminodiphenyl ether. The 3,3'-dinitro-4,4'-diaminodiphenyl ether was then reduced with stannous chloride and hydrochloric acid to give bis(3,4-diaminophenyl)ether.

A mixture of bis(3,4-diaminophenyl)ether (22.00 g, 0.096 mol), phenyl-4-hydroxybenzoate (41.00 g, 0.194 mol), diphenylsulfone (110.17 g), and toluene (135 ml) was heated under a nitrogen atmosphere for 3.5 hours at 150° C. The toluene was removed and the temperature increased to 250° C. and maintained for 1.5 hours. A vacuum was subsequently applied and the temperature increased to 280° C. and maintained for 1.25 hours. The cooled dark reaction mixture was washed in hot toluene and dried at 110° C. to afford 20.59 g (50% crude yield) of a dark purple powder. The dark solid was extracted with acetone to afford 12.39 g (30% yield) of a tan solid. The endothermic peak as determined by DTA was 317° C. (broad). Analysis calcd. for $C_{26}H_{18}N_4O_3$: C, 71.88%; H, 4.18%; N, 12.90%. Found: C, 71.91%; H, 4.22%; N, 13.06%. The resulting monomer had the following structural formula:

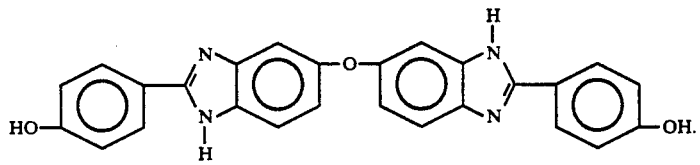

EXAMPLE 2

Into a 100 ml three necked round bottom flask equipped with nitrogen inlet, thermometer, mechanical stirrer, and Dean Stark trap was placed 5,5'-bis[2-(4-hydroxyphenyl)benzimidazole] (2.7835 g, 6.7 mmol), 4,4'-difluorobenzophenone (which is commercially available) (1.4515 g, 6.7 mmol), pulverized anhydrous potassium carbonate (2.4509 g, 17.7 mmol), dry DMAc (22 ml, 18% solids w/w), and toluene (50 ml). The mixture was heated to 140°–150° C. for 3.5 hours and then heated to 155°–160° C. After 2.5 hours the viscous reaction mixture was diluted with 20 ml DMAc (9.7% solids w/w) and stirring continued at 155°-160° C. The viscous reaction mixture was diluted with 25 ml DMAc (6.3% solids w/w) after 1.25 hours. Stirring was continued for 10 minutes at 160° C. and then the reaction mixture cooled. The viscous solution was precipitated in a water/acetic acid (10/1) mixture, washed successively in hot water and methanol and dried at 110° C. to provide a light brown polymer (3.60 g, 91% yield) with a Tg of 307° C. The inherent viscosity of a 0.5% solution in DMAc at 25° C. was 1.11 dL/g. Unoriented thin films cast from a DMAc solution gave tensile strength, tensile modulus, and elongation at 23° C. of 22.8 ksi, 647 ksi, and 11.6%, respectively. Although the activated aromatic dihalide compound contained the halogen fluorine, a chlorine-containing compound may be substituted as is known to those skilled in the art. The resulting polymer had the following structural repeat unit:

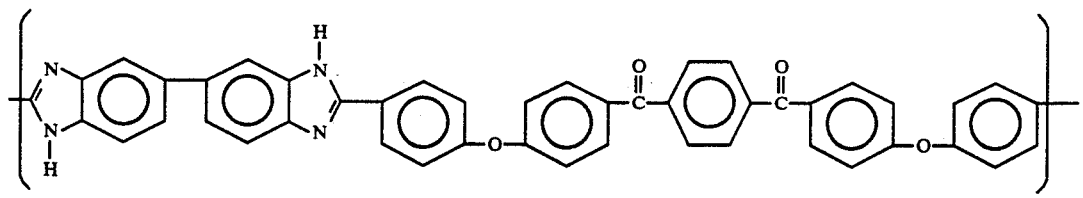

a Tg of 276° C. The inherent viscosity of a 0.5% solution in DMAc at 25° C. was 1.99 dL/g. Unoriented thin films cast from a DMAc solution gave tensile strength, tensile modulus, and elongation at 23° C. of 19.4 ksi, 598 ksi, and 13.1% respectively. The resulting polymer had the following structural repeat unit:

EXAMPLE 4

Into a 100 ml three necked round bottom flask equipped with nitrogen inlet, thermometer, mechanical stirrer, and Dean Stark trap was placed 5,5'-carbonyl-bis[2-(4-hydroxyphenyl)benzimidazole] (2.5651 g, 5.7 mmol), 4,4'-difluorobenzophenone (1.2537 g, 5.7 mmol), pulverized anhydrous potassium carbonate (2.0686 g, 15.0 mmol), dry DMAc (18.5 ml, 18% solids w/w) and toluene (45 ml). The mixture was heated to 140°-150° C. for 3.5 hours and then heated to 155°-160° C. After 1.75 hours the viscous reaction mixture was diluted with 18 ml DMAc (10% solids w/w) and stirring continued at 155°-160° C. The viscous reaction mixture was diluted with 20 ml DMAc (6.7% solids w/w) after 0.25 hour. Stirring was continued for 0.5 hour at 160° C. and the reaction mixture was cooled. The viscous solution was precipitated in a water/acetic acid (10/1) mixture, washed successively in hot water and methanol and dried at 110° C. to provide a pale yellow polymer (3.03 g, 84% yield) with no observable Tg by differential scanning calorimetry. The inherent viscosity of a 0.5% solution in DMAc at 25° C. was 0.93 dL/g. The polymer had the following structural repeat unit:

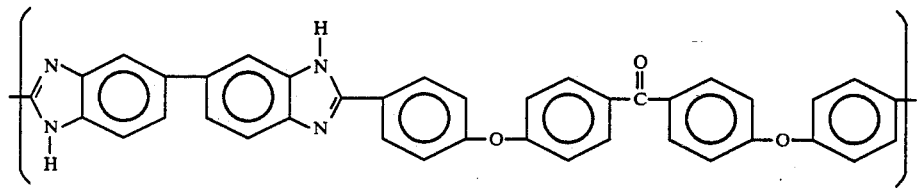

EXAMPLE 3

Into a 100 ml three necked round bottom flask equipped with nitrogen inlet, thermometer, mechanical stirrer, and Dean Stark trap was placed 5,5'-bis[2-(4-hydroxyphenyl)benzimidazole] (2.0392 g, 4.9 mmol), 1,3-bis(4-fluorobenzoyl)benzene (commercially available from Kennedy and Klin) (1.5707 g, 4.9 mmol), potassium carbonate (1.7379 g, 12.6 mmol), dry DMAc (18 ml, 18% solids w/w), and toluene (50 ml). The mixture was heated to 140°-150° C. for 3.5 hours and then heated to 155°-160° C. After approximately 2 hours, the viscous reaction mixture was diluted with 21 ml DMAc (9.0% solids w/w) and stirring continued at 155°-160° C. The viscous reaction mixture was diluted with 25 ml DMAc (5.7% solids w/w) after approximately 0.75 hour. The viscous solution was precipitated in a water/acetic acid (10/1) mixture, washed successively in hot water and methanol and dried at 110° C. to provide a light brown polymer (2.48 g, 73% yield) with

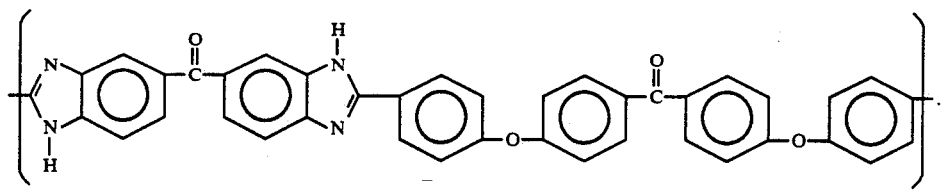

EXAMPLE 5

Into a 100 ml three necked round bottom flask equipped with nitrogen inlet, thermometer, mechanical stirrer, and Dean Stark trap was placed 5,5'-carbonyl-bis[2-(4-hydroxyphenyl)benzimidazole] (2.5712 g, 5.8 mmol), 1,3-bis(4-fluorobenzoyl)benzene (1.8562 g, 5.8 mmol), pulverized anhydrous potassium carbonate (2.200 g, 15.9 mmol), dry DMAc (22 ml, 18% solids w/w), and toluene (50 ml). The mixture was heated to 140°-150° C. for 3.5 hours and then heated to 155°-160° C. After approximately 1.1 hours the viscous reaction mixture was diluted with 20 ml DMAc (10% solids w/w) and stirring continued at 155°-160° C. The viscous reaction mixture was diluted with 20 ml DMAc (7.0% solids w/w) after approximately 0.15 hour. The viscous solution was precipitated in a water/acetic acid (10/1) mixture, washed successively in hot water and methanol and dried at 110° C. to provide a pale yellow polymer (3.13 g, 75% yield) with a Tg of 264° C. The inherent viscosity of a 0.5% solution in DMAc at 25° C. was 1.43 dL/g. Unoriented thin films cast from a DMAc solution gave tensile strength, tensile modulus, and elongation at 23° C. of 19.6 ksi, 612 ksi, and 5.6% respectively. The polymer had the following structural repeat unit:

vide a white polymer (3.60 g, 84% yield) with a Tg of 294° C. The inherent viscosity of a 0.5% solution in DMAc at 25° C. was 1.34 dL/g. Unoriented thin films cast from a DMAc solution gave tensile strength, tensile modulus, and elongation at 23° C. of 19.7 ksi, 576 ksi, and 7.0%, respectively. The resulting polymer had the following structural repeat unit:

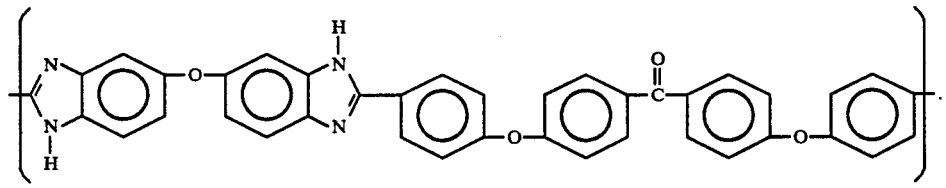

EXAMPLE 7

Into a 100 ml three necked round bottom flask equipped with nitrogen inlet, thermometer mechanical stirrer, and Dean Stark trap was placed 5,5'-oxy-bis[2-(4-hydroxyphenyl)benzimidazole] (2.3330 g, 5.4 mmol), 1,3-bis(4-fluorobenzoyl)benzene (1.7308 g, 5.4 mmol), pulverized anhydrous potassium carbonate (1.9948 g, 14.1 mmol), dry DMAc (19.5 ml, 18% solids w/w), and toluene (45 ml). The mixture was heated to 140°-150° C. for 3.5 hours and then heated to 155°-160° C. After approximately 1 hour the viscous reaction mixture was

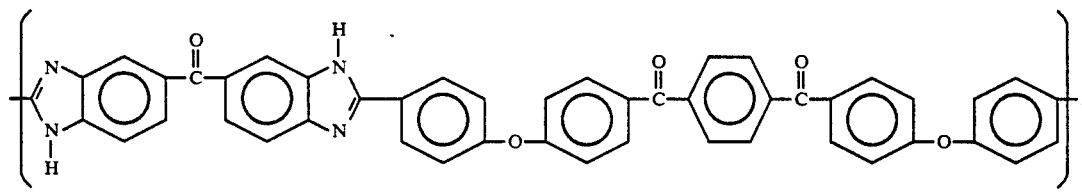

EXAMPLE 6

Into a 100 ml three necked round bottom flask equipped with nitrogen inlet, thermometer, mechanical stirrer, and Dean Stark trap was placed 5,5'-oxy-bis[2-(4-hydroxyphenyl)benzimidazole] (2.9733 g, 6.8 mmol), 4,4'-difluorobenzophenone (1.4933 g, 6.8 mmol), pulverized anhydrous potassium carbonate (2.4468 g, 17.7 mmol), dry DMAc (21.5 ml, 18% solids w/w), and toluene (45 ml). The mixture was heated to 140°-150° C. for 3.5 hours and then heated to 155°-160° C. After approximately 3 hours the viscous reaction mixture was diluted with 20 ml DMAc (10% solids w/w) and stirring continued at 155°-160° C. The viscous reaction mixture was diluted with 25 ml DMAc (6.7% solids w/w) after approximately 1.5 hours. Stirring was continued for 0.25 hour at 160° C. and the reaction mixture was cooled. The viscous solution was precipitated in a water/acetic acid (10/1) mixture, washed successively in hot water and methanol and dried at 110° C. to prodiluted with 20 ml DMAc (9.9% solids w/w) and stirring continued at 155°-160° C. The viscous reaction mixture was diluted with 20 ml DMAc (6.8% solids w/w) after approximately 0.3 hour. Stirring was continued for 5 minutes and the reaction mixture was cooled. The viscous solution was precipitated in a water/acetic acid (10/1) mixture, washed successively in hot water and methanol and dried at 110° C. to provide a white polymer (3.13 g, 75% yield) with a Tg of 269° C. The inherent viscosity of a 0.5% solution in DMAc at 25° C. was 1.79 dL/g. Unoriented thin films cast from a DMAc solution gave tensile strength, tensile modulus, and elongation at 23° C. of 18.4 ksi, 591 ksi, and 6.1%, respectively. The resulting polymer had the following structural repeat unit:

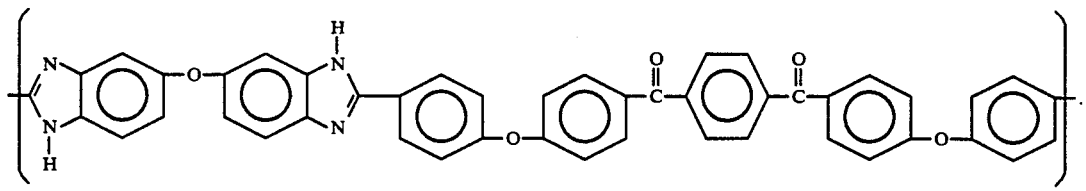

Although these polymers were made using DMAc as the solvent, other solvents known to those skilled in the art, such as N-methyl-pyrrolidinone, diphenylsulfone, and sulfolane may also be used.

In addition to the polymers made in the foregoing examples, additional polymers were made and their properties are tabulated in Tables 1 and 2.

TABLE 1
POLYMER CHARACTERIZATION

| Y | X | η inh,[1] dL/g | $T_g$,[2] °C. | Temp. of 5% wt. loss, °C.[3] air | N2 |
|---|---|---|---|---|---|
| SO$_2$ | nil | 1.87 | 352 | 441 | 456 |
|  | O | 1.42 | 322 | 435 | 451 |
|  | CO | 0.93 | N.D.[4] | 422 | 433 |
|  | nil | 1.11 | 307 | 466 | 502 |
|  | O | 1.34 | 294 | 442 | 489 |
|  | CO | 0.93 | N.D.[4] | 433 | 451 |
| 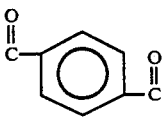 | nil | 1.19 | 295 | 469 | 520 |
|  | O | 1.23 | 282 | 469 | 490 |
|  | CO | 0.79 | 276 | 444 | 478 |
| 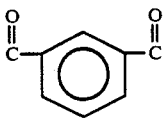 | nil | 1.99 | 276 | 476 | 515 |
|  | O | 1.79 | 269 | 454 | 499 |
|  | CO | 1.43 | 264 | 467 | 489 |

[1] Inherent viscosity measured in DMAc on 0.5% (w/v) solutions at 25° C.
[2] Glass transition temperature determined by DSC at a heating rate of 20° C./min
[3] TGA measured on powdered samples at a heating rate of 2.5° C./min after preheat sample to 180° C. and holding for 0.5 h before analysis
[4] Not detected

TABLE 2
UNORIENTED THIN FILM TENSILE PROPERTIES AT 23° C.*

| Y | X | η inh, dL/g | Strength, ksi | Modulus, ksi | Elong. at break, % |
|---|---|---|---|---|---|
| SO$_2$ | nil | 1.87 | 22.5 | 652 | 9.3 |
|  | O | 1.42 | 18.8 | 569 | 7.6 |
|  | nil | 1.11 | 22.8 | 647 | 11.6 |
|  | O | 1.34 | 19.7 | 576 | 7.0 |
| 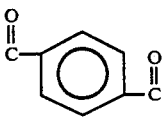 | nil | 1.19 | 20.2 | 605 | 14.3 |
|  | O | 1.23 | 17.6 | 539 | 18.0 |
| 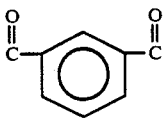 | nil | 1.99 | 19.4 | 598 | 13.1 |
|  | O | 1.79 | 18.4 | 591 | 6.1 |
|  | CO | 1.43 | 19.6 | 612 | 5.6 |

*Films dried at 100, 200, and ~50° C. above their respective Tg in an air oven

What is claimed is:

1. A soluble polybenzimidazole having the following structural repeat unit:
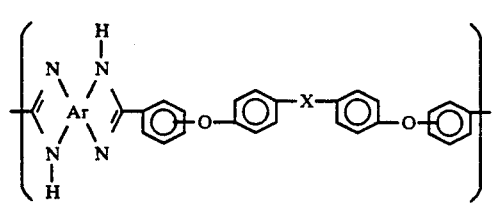
where:
the catenation of oxygen is selected from the group consisting of: meta-meta, para-para, and para-meta;
Ar is selected from the group consisting of:
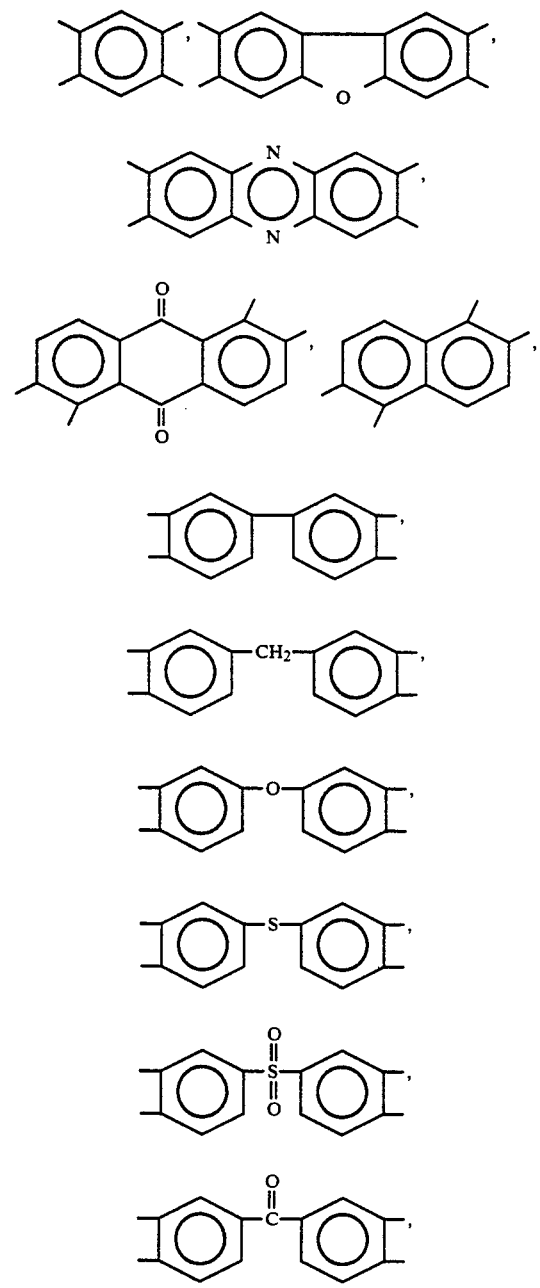
x is selected from the group consisting of:
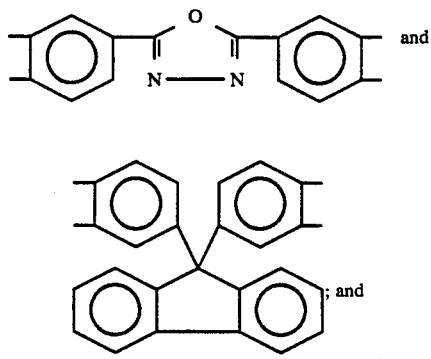
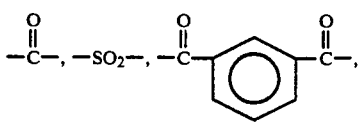
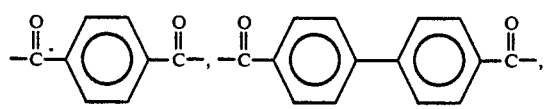
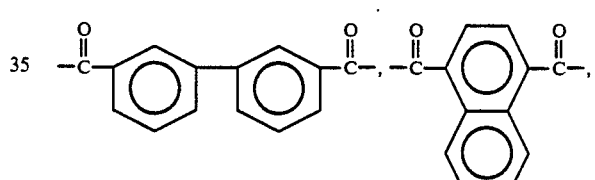
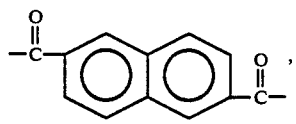
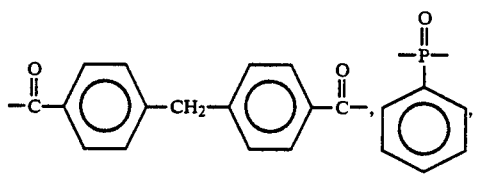
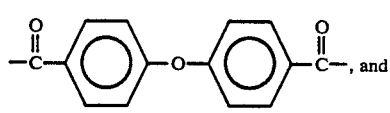
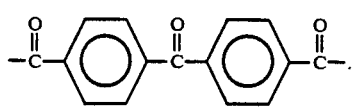
2. A soluble polybenzimidazole of claim 1, having the following structural repeat unit:

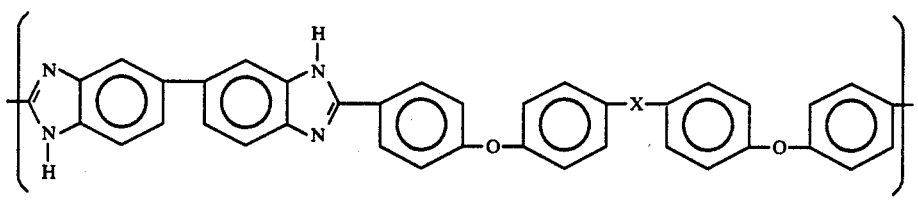

where x is selected from the group consisting of:

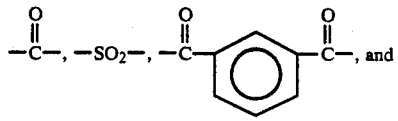

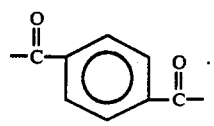

3. A soluble polybenzimidazole of claim 1, having the following structural repeat unit:

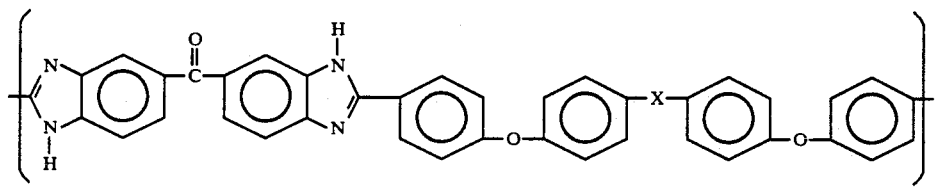

where x is selected from the group consisting of:

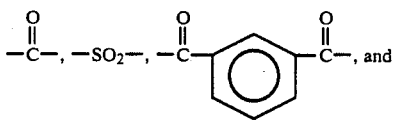

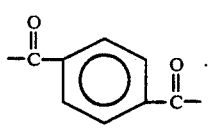

4. A soluble polybenzimidazole of claim 1, having the following structural repeat unit:

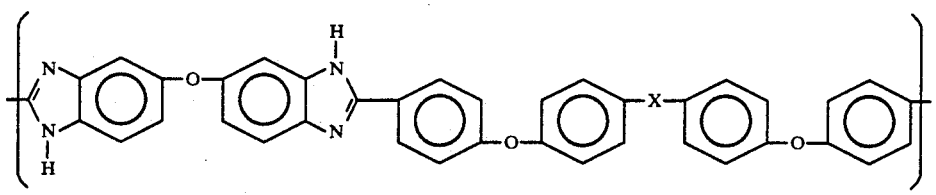

where x is selected from the group consisting of:

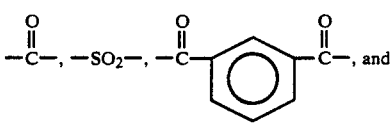

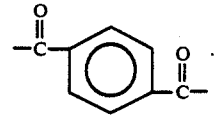

5. A film prepared from the polybenzimidazole of claim 1.

6. A process to prepare the soluble polybenzimidazole of claim 1, comprising the steps of:
   a. forming a mixture comprising a di(hydroxyphenyl)benzimidazole monomer, an activated aromatic dihalide compound, an alkali metal base selected from the group consisting of: potassium carbonate, sodium carbonate, potassium hydroxide, and sodium hydroxide; and a solvent selected from the group consisting of: N,N-dimethylacetamide, N-methyl-pyrrolidinone, diphenylsulfone, and sulfolane.
   b. heating the mixture to about 150°-200° C.; and
   c. recovering the polymer product.

7. The process of claim 6, wherein said alkali metal base is potassium carbonate.

8. The process of claim 6, wherein the dihalide compound contains a halogen selected from the group consisting of: chlorine and fluorine.

9. A process to prepare the soluble polybenzimidazole of claim 1, comprising the steps of:
   a. forming a mixture comprising a di(hydroxyphenyl)benzimidazole monomer, an activated aromatic dinitro compound, an alkali metal base selected from the group consisting of: potassium carbonate, sodium carbonate, potassium hydroxide, and sodium hydroxide; and a solvent selected from the group consisting of: N,N-dimethylacetamide, N-methyl-pyrrolidinone, diphenylsulfone, and sulfolane.
   b. heating the mixture to about 150°-200° C.; and
   c. recovering the polymer product.

* * * * *